United States Patent
Schainholz et al.

(10) Patent No.: US 7,364,210 B2
(45) Date of Patent: *Apr. 29, 2008

(54) TAMPER-PROOF SEAL AND METHOD FOR USING SAME

(75) Inventors: Jay D. Schainholz, Cliffside Park, NJ (US); Eugene Ogman, South Salem, NY (US); Amos Shamir, New York, NY (US)

(73) Assignee: Medin Corporation, Passaic, NJ (US)

( * ) Notice: Subject to any disclaimer, the term of this patent is extended or adjusted under 35 U.S.C. 154(b) by 425 days.

This patent is subject to a terminal disclaimer.

(21) Appl. No.: 11/064,554

(22) Filed: Feb. 24, 2005

(65) Prior Publication Data

US 2005/0139599 A1    Jun. 30, 2005

Related U.S. Application Data

(60) Division of application No. 10/226,982, filed on Aug. 23, 2002, now Pat. No. 6,880,869, which is a continuation-in-part of application No. 09/534,273, filed on Mar. 23, 2000, now Pat. No. 6,439,625.

(51) Int. Cl.
    *B65D 27/30*    (2006.01)

(52) U.S. Cl. .................. 292/307 A; 292/315; 422/119; 116/207; 436/1

(58) Field of Classification Search ............ 292/307 A, 292/307 B, 307 R, 318, 315, 325; 206/439; 116/207; 374/102; 422/26, 119, 301; 436/1
    See application file for complete search history.

(56) References Cited

U.S. PATENT DOCUMENTS

| | | | |
|---|---|---|---|
| 3,733,002 A | * | 5/1973 | Fujio ........................ 215/12.2 |
| 4,059,300 A | * | 11/1977 | Moberg et al. ............. 292/322 |
| 4,135,868 A | | 1/1979 | Schainholz |
| 4,289,088 A | | 9/1981 | Scibelli |
| 4,331,257 A | | 5/1982 | Taschner |
| 4,349,118 A | | 9/1982 | Sanderson |
| 4,550,842 A | | 11/1985 | Cummings |
| 4,562,047 A | | 12/1985 | Sestak et al. |
| 4,584,182 A | | 4/1986 | Sanderson |
| 4,625,885 A | | 12/1986 | Nichols |
| 4,661,326 A | | 4/1987 | Schainholz |
| 4,706,839 A | | 11/1987 | Spence |

(Continued)

FOREIGN PATENT DOCUMENTS

WO    WO-01/70581    9/2001

*Primary Examiner*—Gary Estremsky
(74) *Attorney, Agent, or Firm*—Lerner, David, Littenberg, Krumholz & Mentlik, LLP

(57) ABSTRACT

A tamper-proof seal is disclosed for use in connection with sterilization containers. The seal includes a body portion including a sterilization indicating material and a tongue extending from the body portion. The tongue may be in the form of a laminate consisting of a pair of substantially inert outer layers sandwiching a high shrink inner layer. The tongue is designed to engage the latch mechanism of a sterilization container when the container is in the closed position and the latch mechanism is in a latched position. Upon exposure of the container to sterilization conditions, the tongue shrinks, causing the outer layers to fold upon themselves to form at least one pleat. The container latch mechanism cannot be opened without fracturing the tongue of the seal, thereby providing visible evidence of the latch mechanism being opened.

25 Claims, 9 Drawing Sheets

U.S. PATENT DOCUMENTS

| | | |
|---|---|---|
| 4,783,321 A | 11/1988 | Spence |
| 4,820,499 A | 4/1989 | Taschner |
| 4,863,453 A | 9/1989 | Berger |
| 4,915,913 A | 4/1990 | Williams |
| 4,919,888 A * | 4/1990 | Spence ........................ 422/26 |
| 5,153,036 A | 10/1992 | Sugisawa |
| 5,169,188 A | 12/1992 | Kupperman et al. |
| 5,225,162 A | 7/1993 | Scoville |
| 5,286,110 A | 2/1994 | Benson et al. |
| 5,328,661 A | 7/1994 | Taschner |
| 5,382,528 A | 1/1995 | Scoville |
| 5,508,006 A | 4/1996 | Gabele et al. |
| 5,531,695 A | 7/1996 | Swisher |
| 5,560,657 A | 10/1996 | Morgan |
| 5,725,830 A | 3/1998 | Taschner |
| RE36,062 E | 1/1999 | Speelman |
| 6,217,835 B1 | 4/2001 | Riley et al. |

\* cited by examiner

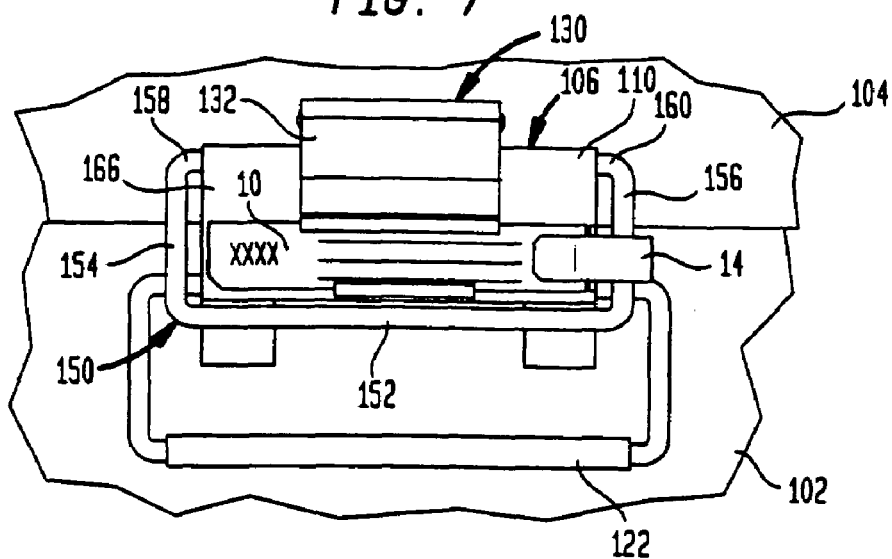
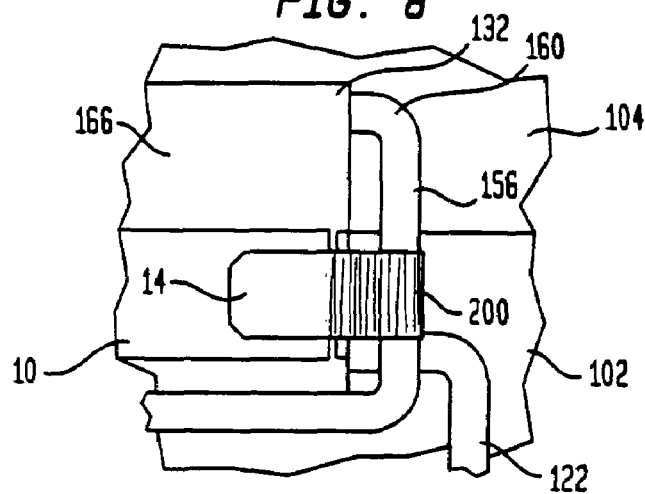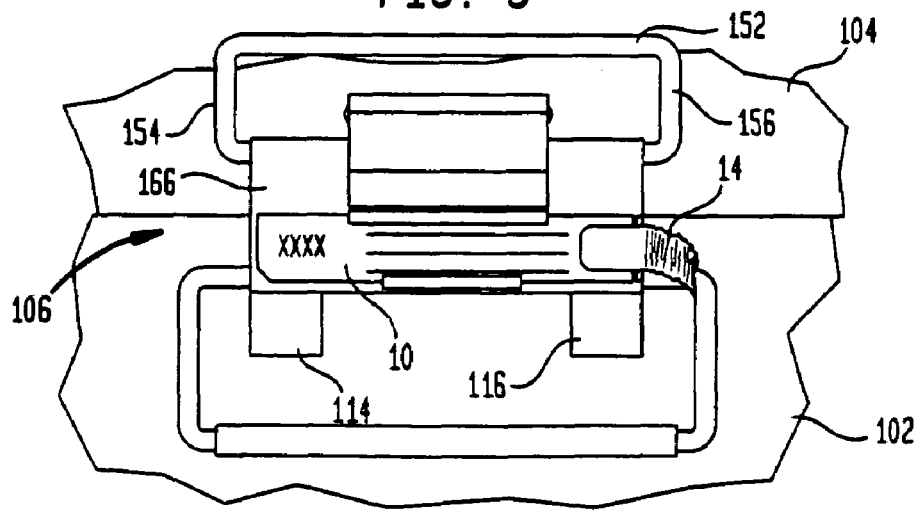

TAMPER-PROOF SEAL AND METHOD FOR USING SAME

CROSS-REFERENCE TO RELATED APPLICATIONS

The present application is a divisional application of application Ser. No. 10/226,982 filed on Aug. 23, 2002, now U.S. Pat. No. 6,880,869 which is a continuation-in-part of application Ser. No. 09/534,273 filed on Mar. 23, 2000, now U.S. Pat. No. 6,439,625, the disclosures of which are hereby incorporated by reference herein.

FIELD OF THE INVENTION

The present invention is generally directed to sterilization containers, and, more particularly, to a tamper-proof seal for providing an indication of whether the container has been opened subsequent to a sterilization process.

BACKGROUND OF THE INVENTION

The sterilization of medical instruments is an important factor in preventing infection and the spread of disease. In this regard, specialized sterilization containers have been developed to facilitate sterilization and the storage of sterilized articles in such a manner that their sterilized state is maintained during storage. These containers generally permit entry of the sterilizing medium into the container during the sterilization process, but prevent the entry of airborne contaminants once closed.

In order to provide evidence that the contents of a container have been through a proper sterilization cycle, a removable or permanent tag, tape, label or other device is frequently provided on the exterior of the container. The label or other device may include an ink or other indicator which changes in appearance to demonstrate exposure to conditions sufficient to effect proper sterilization of the container contents. Thus, the intention of these devices is to provide assurances that, when the device on a container has changed in appearance, the container has gone through a proper sterilization cycle. This purpose is easily circumvented, however, simply by processing the device through a sterilization cycle prior to placing it on a container, giving the appearance that the entire container has been through the sterilization cycle.

Another deficiency in the use of these devices stems from the fact that, once the sterilization process has been completed, containers containing sterilized articles are frequently stored for relatively long periods of time before the articles are needed. During this storage period, there is a possibility that the container will be opened, causing contamination of the articles, and then subsequently reclosed. Such unauthorized opening of the container is not readily revealed by visual inspection, and could lead to the use of articles that are no longer sterile or that, perhaps, were never sterilized. Thus, while indicator devices potentially may show that a particular container has been subjected to a sterilization process sufficient to sterilize the articles contained therein, they cannot provide evidence as to whether the articles have become contaminated at any time subsequent to sterilization.

In order to provide evidence of the sterile integrity of the contents of these containers once a sterilization procedure has been completed, various devices have been developed which provide a visual indication that the container may have been opened. Typically, these devices include a seal which must be destroyed to unlock the locking mechanism which enables the container to be opened. Therefore, it can be assumed that, for any container having a broken or missing seal, the contents of the container are no longer sterile. Many of these devices, however, simply prevent the container from being opened, but provide no positive indication as to whether the container has been subjected to a complete sterilization process. Other devices may visually indicate that sterilization has taken place, but provide no region for inscribing data relative to the container and its contents. As a result, the use of these devices frequently requires additional elements to be used to record data relative to the container and/or to indicate that the container has been subjected to a sterilization process.

There therefore exists a need for a security device that enables the recordation of data relative to the contents of the container or other relevant data, that provides a reliable visual indication that the container has been subjected to a sterilization process, and that also reliably reveals whether the container has been opened subsequent to the sterilization process.

SUMMARY OF THE INVENTION

The present invention addresses these needs.

One aspect of the present invention provides a disposable seal for a container having a latch mechanism. In one embodiment, the seal includes a body and a tongue having one end connected to the body and a free end. The tongue includes a layer of a shrinkable material, preferably, a heat shrinkable material, such as a heat shrink vinyl. A weakened region may be formed between the body and the tongue to define a region where these elements may be separated from one another subsequent to a sterilization process.

In preferred embodiments, the body of the seal may include a sterilization indicator material. Such sterilization indicator material may consist of a sterilization indicating ink.

The free end of the tongue may initially be remote from the body, but be adhered to the body during use of the seal. An adhesive may be provided on the free end of the tongue to keep the tongue adhered to the body during sterilization.

The tongue may have an initial length and a length after sterilization which is less than the initial length. Desirably, the initial length of the tongue is sufficient to permit the tongue to be assembled to the latch mechanism of the container in a use position, but the length of the tongue after sterilization is not sufficient to permit such assembly.

In highly preferred embodiments hereof, the shrinkable material has first and second surfaces, and the tongue may include at least one layer of a second material laminated to the first surface of the shrinkable material. The second material may include a weakened region between the one end of the tongue and the free end thereof. The tongue may have a longitudinal direction between the one end and the free end thereof, and the weakened region may include a series of at least three perforations in the second material, the perforations extending in a direction transverse to the longitudinal direction. An adhesive may be provided for adhering the second material to the shrinkable material. Preferably, the adhesive is not provided in the weakened region.

A layer of a third material may be laminated to the second surface of the shrinkable material so that the shrinkable material is disposed between the second and third materials. The second and third materials each may include a weakened region between the one end of the tongue and the free end thereof. The weakened regions in both the second material and the third material may include a series of at least three perforations, the perforations extending in a direction transverse to the longitudinal direction. Preferably, the perforations in the second material are in registry with the perforations in the third material.

The second and third materials may be selected from the group consisting of polymers and, in particular, polyolefins. Moreover, the second and third materials may be the same. Where at least one layer of a second material is laminated to the shrinkable material, the tongue preferably has an initial thickness and a thickness after sterilization which is greater than the initial thickness. Moreover, the tongue preferably has a selected width, and the body has a width which is greater than the selected width.

Another embodiment of the seal in accordance with this aspect of the present invention consists of a body including a sterilization indicator material and a tongue having one end connected to the body and a free end. The sterilization indicator material may consist of a sterilization indicating ink. The tongue has an initial length and a length after sterilization which is less than the initial length.

A further embodiment of the seal in accordance with this aspect of the present invention consists of a body including a sterilization indicator material and a tongue having one end connected to the body and a free end. The tongue has an initial thickness and a thickness after sterilization which is greater than the initial thickness.

A further aspect of the present invention provides methods for safeguarding the sterility of a sterilization container having a base, a lid matable with the base in sealing engagement, and a latch mechanism having a latched position for locking the lid to the base and an unlatched position for releasing the lid for removal from the base. In accordance with the methods, articles to be sterilized are placed in the base and the lid is applied to close the base. The latch mechanism may then be placed in the latched position to lock the lid to the base. Subsequently, a seal may be assembled to the latch mechanism to obstruct the free movement of the latch mechanism from the latched position to the unlatched position. In accordance with one method, the seal has a body including a sterilization indicator material and a tongue having at least one end connected to the body and a free end. As the container is processed through a sterilization treatment, the tongue shrinks to maintain the latch mechanism in the latched position, and a property of the sterilization indicator material changes to indicate completion of sterilization. After sterilization, the latch mechanism may be moved to the unlatched position to release the lid from the base, the movement of the latch mechanism from the latched position to the unlatched position breaking the tongue of the seal.

In another method, the seal has a body and a tongue having at least one end connected to the body and a free end. Upon processing the container through a sterilization treatment, the tongue increases in thickness to maintain the latch mechanism in the latched position. Moving the latch mechanism from the latched position to the unlatched position to release the lid from the base causes the tongue of the seal to break.

BRIEF DESCRIPTION OF THE DRAWINGS

A more complete appreciation of the subject matter of the present invention and the various advantages thereof can be realized by reference to the following detailed description in which reference is made to the accompanying drawings in which:

FIG. 7 is an enlarged view showing the seal of FIG. 2 on the sterilization container prior to a sterilization procedure;

FIG. 8 is a view similar to FIG. 7, showing the seal of FIG. 2 subsequent to a sterilization procedure;

FIG. 9 is a view similar to FIG. 7, showing the fracture of the seal upon opening the container latch mechanism;

DETAILED DESCRIPTION OF THE PREFERRED EMBODIMENTS

Figure 1:
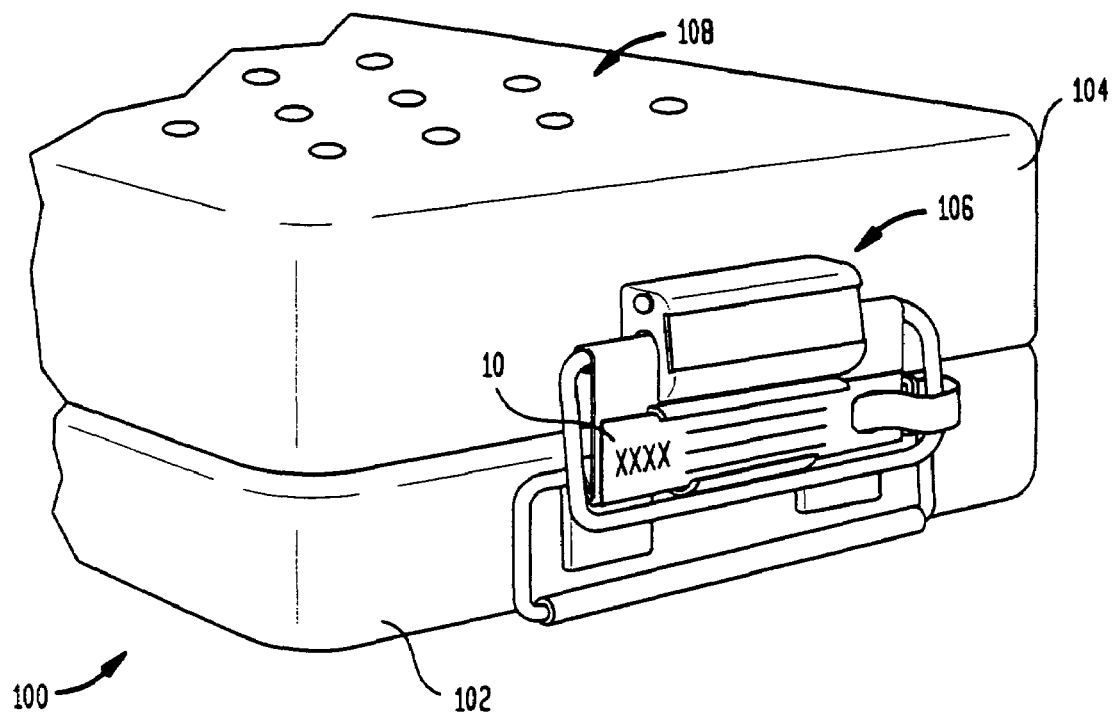
FIG. 1 is a perspective view of a sterilization container incorporating the seal of the present invention.
Figure 2:
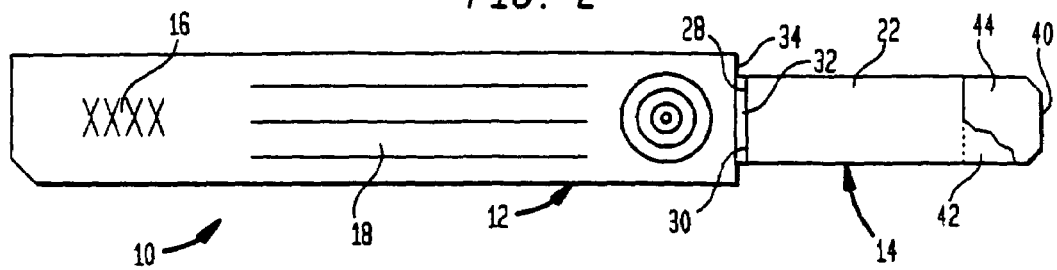
FIG. 2 is a front elevational view of a first embodiment of the seal of the present invention.
Figure 3:
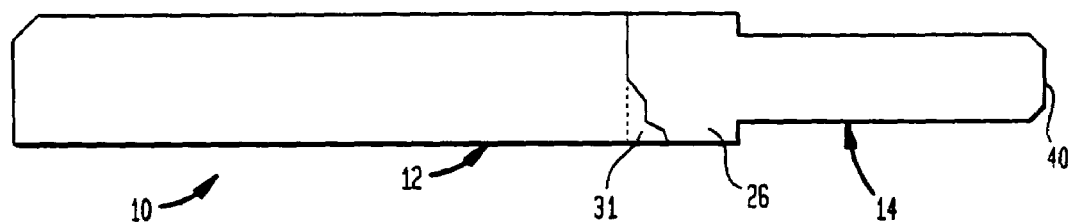
FIG. 3 is a rear elevational view of the seal of FIG. 2.

In the following, a tamper-proof seal is described for use in conventional steam sterilization processes. Such processes typically subject a sterilization container and its contents to a temperature of about 270° F. for about four minutes in a pressurized steam autoclave. It will be appreciated, however, that the present invention may be used in connection with other known types of sterilization processes, including gas (e.g., ozone or ethylene oxide) sterilization, dry heat sterilization, paracetic acid sterilization, ultraviolet or gamma radiation sterilization or gas plasma/hydrogen peroxide sterilization processes.

A first preferred embodiment of a tamper-proof seal 10 in accordance with the present invention is illustrated in FIGS.

2-4. Seal 10 generally includes a body portion 12 and a severable tongue 14 projecting from one end thereof. Body portion 12 may be formed from a conventional paper, paperboard, card stock or similar material, and includes a first field or region 16 to which may be applied a conventional sterilization indicator material, such as a steam and/or gas sterilization indicating ink available from Tempil, Inc. of South Plainfield, N.J. Such inks typically change color upon exposure to steam or a gas at sterilizing conditions. Body portion 12 may also include a second region 18 having spaces for receiving variable data regarding the contents of the sterilization container, the date of sterilization, the operator, etc. Further fields may be printed with instructions for use, manufacturer information and the like.

Figure 4:
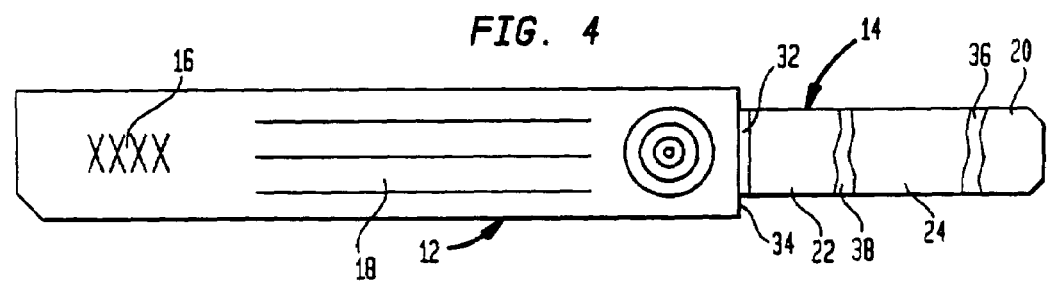
FIG. 4 is a front elevational view of the seal of FIG. 2, partially broken away to show the layers forming the tongue portion thereof.
Figure 5:
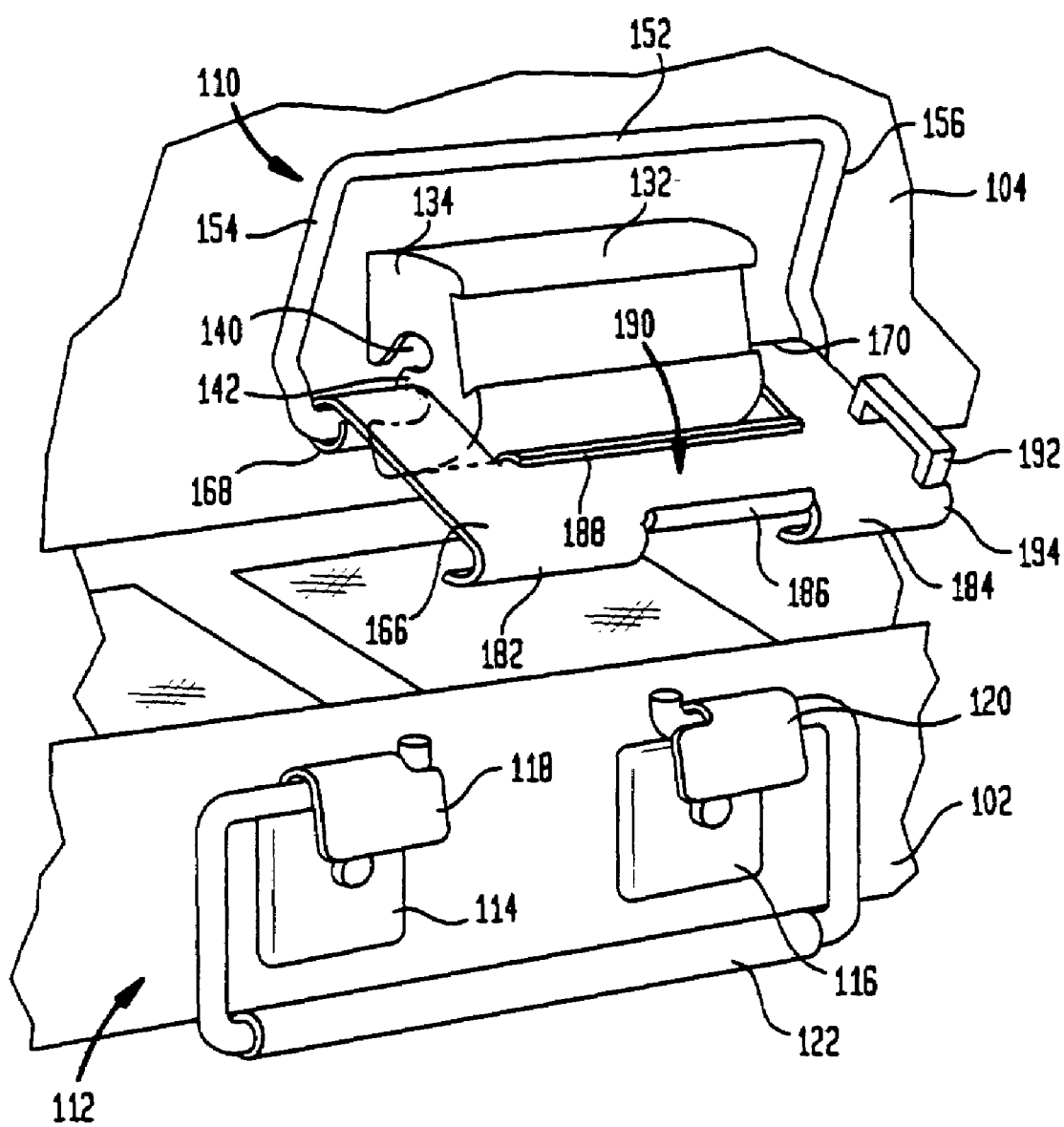
FIG. 5 is an enlarged perspective view showing the latch mechanism of the sterilization container of FIG. 1 in an open position.
Figure 6:
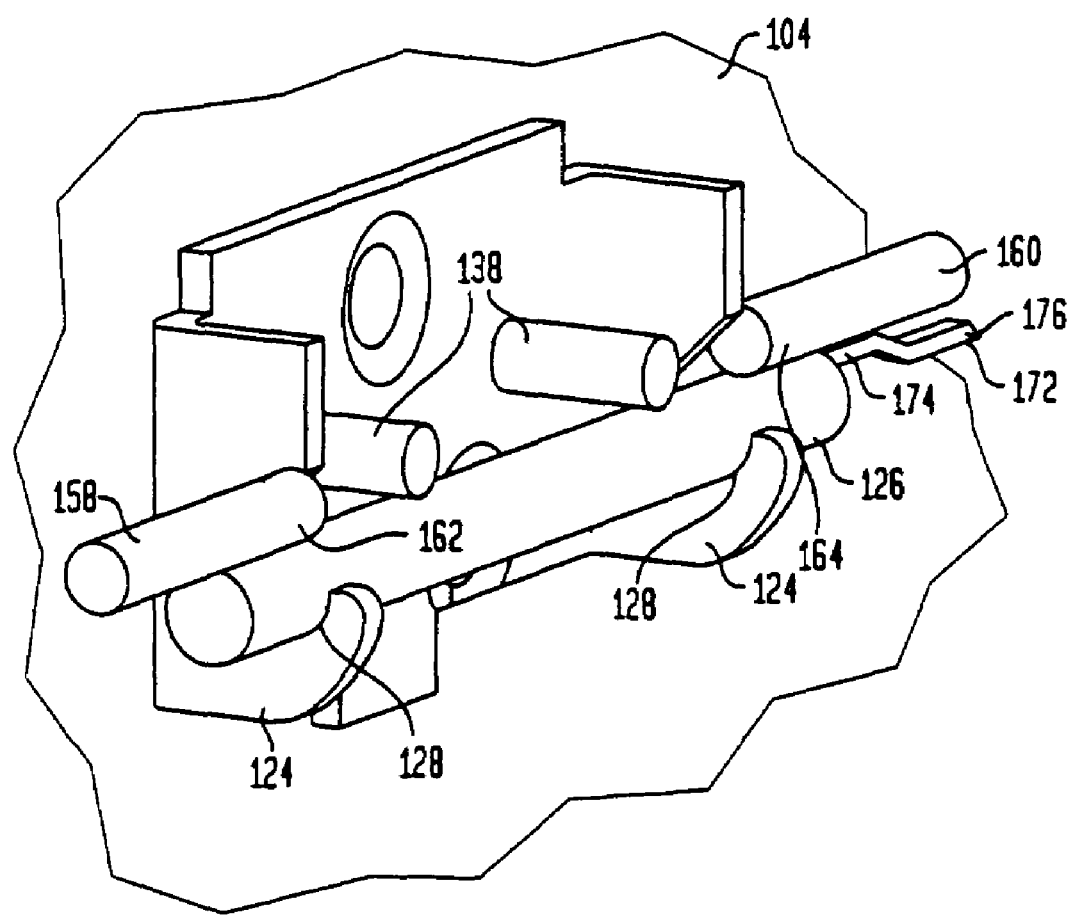
FIG. 6 is an enlarged perspective view showing the inner structure of the latch mechanism.

Referring to FIG. 4, tongue 14 may be a multi-ply laminate consisting of a pair of outer layers 20 and 22 sandwiching an inner layer 24 of a high shrinkage material. Preferably, the layers are assembled so that layer 20 has an enlarged end portion 26 which extends beyond the ends 28 and 30 of layers 22 and 24, respectively. End portion 26 may be connected to body portion 12 using an adhesive 31 which will maintain its adhesive properties when exposed to the temperature and environmental conditions of the sterilization process. An example of an adhesive which may be useful for this purpose is a pressure sensitive acrylic adhesive. Where layer 20 is a polymer, it may be anhydride grafted in a known fashion to provide the requisite adhesion properties for adherence of end portion 26 to body portion 12. Alternatively, end portion 26 of layer 20 may be connected to body portion 12 mechanically, such as by stapling, sewing, riveting or the like, or by heat welding, ultrasonic welding, radio frequency sealing, embossing or other such techniques. Preferably, end portion 26 is connected to body portion 12 so as to create a gap 32 between the end 34 of body portion 12 and the ends 28 and 30 of layers 22 and 24. Gap 32 provides a weakened region enabling tongue 14 to be separated from body portion 12, as described hereinbelow. Alternatively, the ends 28 and 30 of layers 22 and 24 may extend to or beyond the end 34 of body portion 12, and a series of perforations (not shown) may be formed in tongue 14 adjacent end 34 of body portion 12 to facilitate the separation of tongue 14 from the body portion of the seal. It will be appreciated, of course, that gap 32 also may include perforations to make it easier to separate tongue 14 from body portion 12.

Outer layers 20 and 22 may be formed from any film which is substantially inert to the sterilization conditions and which is sufficiently flexible as to not interfere with the shrinkage of layer 24 during sterilization. Such materials may include, for example, thin, flexible papers; polymer and copolymer films, including those formed from polyester, polystyrene, polyurethane, polyamides, polyethylene, polypropylene, polyolefins, polytetrafluoroethylene, vinyls or the like; and polymer/paper composites, such as the polymer/paper composite sold under the trademark Kindura #50 by Lindenmeyr Paper Corporation. Preferred are soft, flexible polyolefin films and vinyl films which do not substantially shrink under the sterilization conditions, but which form smooth pleats as layer 24 shrinks therebetween. A particularly preferred material for forming layers 20 and 22 is a polyolefin film having a thickness of about 0.0025 inches. The materials for forming layers 20 and 22 need not be the same. However, forming layers 20 and 22 from the same material is preferred since these layers will behave the same during the sterilization process, and therefore will prevent the development of undue stresses in tongue 14 as it shrinks.

Layer 24 may be formed from a material which shrinks in response to a condition encountered during the sterilization process. For steam or heat sterilization, for example, such materials may include polymeric films which shrink in length when exposed to the sterilization temperature. Included among these materials are films that, after fabrication, are expanded in the length direction and cured in the expanded condition. Such films have a memory such that, upon reaching a critical temperature, the films rapidly revert to their original length. Preferably, such films shrink by at least 25% of their original length; more preferably, by at least about 40% of their original length. The amount of shrinkage desired, however, will depend upon the initial length of tongue 14 as well as the particular latch mechanism with which seal 10 is used. Preferred shrink films include those known generally as heat shrink vinyls which shrink to about 40-60% of their original length. A particularly preferred shrink film is a self-adhesive film sold under the name Transcode by Avery Dennison Corporation of Pasadena, Calif.

Layers 20 and 22 may be laminated to layer 24 by adhesive layers 36 and 38, respectively. Layers 36 and 38 may be provided as integral adhesive coatings on the surface of layers 20, 22 and/or 24, may be formed from the same adhesive as adhesive 31 used to secure end portion 26 of layer 20 to body portion 12, or may be a different adhesive capable of bonding layers 20 and 22 to layer 24.

The portion of tongue 14 adjacent its free end 40 may include a layer of an adhesive 42 for adhering end 40 to body portion 12 in the use condition of seal 10. Adhesive 42 preferably is a conventional high temperature adhesive which will convert during the sterilization process to a form which will keep end 40 of tongue 14 firmly secured to body portion 12, but which is no longer adhesive and therefore will not allow the tongue to first be adhered to the body portion. This will prevent a person from subjecting the tamper-proof seal to a sterilization process apart from a sterilization container, and then applying the seal to a container which has not been sterilized. Preferred adhesives in this regard may include unsupported acrylic adhesives, such as adhesive 9458 available from Minnesota Mining and Manufacturing Company of St. Paul, Minn. A conventional release layer 44 may be applied over adhesive 42 in order to protect the adhesive during shipping, storage and handling of seal 10.

One embodiment of a sterilization container 100 with which the tamper-proof seal of the present invention may be used is illustrated in FIG. 1. Container 100 generally has a construction which is similar to sterilization containers known in the art, and includes a base portion or receptacle 102 and a top portion or lid 104 which is sealably clamped to receptacle 102 by a pair of latch mechanisms 106 (only one of which is illustrated), one on each end of the container. Receptacle 102 and lid 104 both may include a series of perforations 108 formed therein (only the perforations on lid 104 being shown), with a filter material (not shown) assembled to an interior surface thereof overlying the perforations. The filter material may be any well-known material that permits the passage of sterilizing media and air therethrough but prevents the passage of microbial contamination. A plurality of feet (not shown) may project from the bottom of receptacle 102 to space the bottom of the container from the support surface, thereby permitting the sterilizing media and air to pass into the container from the bottom.

One of latch mechanisms 106 is shown in more detail in FIGS. 5-9. Latch mechanism 106 generally includes an actuating portion 110 connected to lid 104, and a passive portion 112 connected to receptacle 102. Passive portion 112 may consist of a pair of spaced apart brackets 114 and 116 bolted, welded or otherwise connected to an end of receptacle 102. Brackets 114 and 116 each include an outwardly and downwardly facing hook member, as at 118 and 120, respectively. Optionally, each pair of brackets 114 and 116 may also mount a pivotable carrying handle 122 to an end of receptacle 102.

Actuating portion 110 includes a pair of spaced support arms 124 mounted to an end wall of lid 104 by rivets, welding, screws or another known fastening mechanism. A shaft 126 is mounted in generally U-shaped recesses 128 formed in the free ends of support arms 124. Shaft 126 is mounted for rotation about a horizontal axis of rotation extending parallel to the end wall of the container.

Support arms 124 and shaft 126 are enclosed by a housing 130 having a central portion 132 and a pair of end plates 134 (only one of which is shown) connected to the central portion. Central portion 132 is fastened to lid 104 by a pair of bolts 138 which are positioned so as to block the movement of shaft 126 out from recesses 128. End plates 134 each include an arcuate cutout 140 defining a tab 142 axially aligned with shaft 126. The tabs 142 on either side of housing 130 prevent shaft 126 from moving axially out of the housing.

Actuating portion 110 further includes an operating handle 150 having a grasping portion 152 connected by sides 154 and 156 to return portions 158 and 160. The return portions 158 and 160 are welded or otherwise connected at their ends 162 and 164, respectively, in a side-by-side arrangement to the circumferential surface at the ends of shaft 126. As a result, the movement of operating handle 150 from the downward facing latched position depicted in FIGS. 7 and 8 to the unlatched position depicted in FIG. 9 causes shaft 126 to rotate within recesses 128. The rotation of shaft 126, in turn, causes the return portions 158 and 160 of operating handle 150 to travel through a circular path around the axis of rotation of shaft 126, which path is eccentric relative to receptacle 102. Cutouts 140 in end plates 134 provide clearance for return portions 158 and 160 to move through the circular path.

A latch plate 166 is hingedly connected to the return portions 158 and 160 of operating handle 150 between the sides 154 and 156 thereof and end plates 134. This hinged connection may be made, for example, by bending the end portions 168 and 170 of latch plate 166 around return portions 158 and 160, respectively. A stop finger 172 may have one end 174 welded or otherwise connected to return portion 160 adjacent its end 164, and a free end 176 spaced from return portion 160 so that the bent portion 170 of latch plate 166 can move freely between the free end 176 and return portion 160. Stop finger 172 is positioned so as to interfere with the rotation of operating handle 150 relative to latch plate 166 once the latch plate has been released from its locked position so that continued rotation of operating handle 150 causes latch plate 166 to pivot outwardly.

On its free edge 180, the end edge portions of latch plate 166 may be bent inwardly and upwardly to define hook members 182 and 184 which, as described below, mate with hook members 118 and 120 on receptacle 102 to hold lid 104 in sealed engagement to receptacle 102. Between hook members 182 and 184, the free edge 180 of latch plate 166 may be bent outwardly and upwardly to define hook member 186. Hook member 186 cooperates with an outwardly and downwardly bent hook member 188 to define a slot 190 for slidably receiving the body portion 12 of tamper-proof seal 10 and to hold the body portion in assembled position on latch plate 166. One end of latch plate 166 may also include an outwardly bent tab 192 defining a rectangular aperture 194 in axial alignment with slot 190. Aperture 194 has a width sufficiently large to receive tongue 14 therethrough, but sufficiently narrow so as to prevent the passage of body portion 12.

In the use of the sterilization system of the present invention, medical instruments or other articles to be sterilized are placed in receptacle 102, and lid 104 is assembled thereover. The latch mechanisms 106 on the ends of container 100 may then be operated to lock lid 104 to receptacle 102. This may be accomplished by pulling operating handles 150 upward, resulting in the downward movement of latch plates 166 until hook members 182 and 184 are aligned under hook members 118 and 120 on receptacle 102. Subsequently, operating handles 150 may be rotated downward, resulting in an upward movement of latch plates 166 until hook members 182 and 184 engage hook members 118 and 120. When operating handles 150 are moved to the fully downward position, latch mechanisms 106 will lock in place, locking lid 104 to receptacle 102.

Once container 100 has been closed and latch mechanisms 106 moved to the locked position, a tamper-proof seal 10 in accordance with the first embodiment of the present invention may be assembled to the latch mechanism on one side of the container, and preferably to the latch mechanism on both sides of the container. Seal 10 is assembled to latch plate 166 by first orienting the seal so that region 16 containing the sterilization indicating material faces away from the container and then guiding tongue 14 through aperture 194 as the body portion 12 of the seal is slid into slot 190. Body portion 12 is advanced until its end 34 abuts tab 192. The release layer 44 at the free end 40 of tongue 14 may then be removed, exposing the adhesive 42 thereunder, and the tongue may be folded around and over side 156 of operating handle 150, whereupon its free end may be adhered to body portion 12, as shown in FIG. 7. When assembled to latch plate 166 in this manner, regions 16 and 18 will face away from container 100, such that any sterilization indicator materials and data printed in these regions will be fully visible to a technician. Also, tongue 14 in this assembled position fits loosely around side 156 of operating handle 150 such that there is a substantial amount of free space therebetween.

Container 100 may then be exposed to a conventional sterilization process as is known in the art. When the process reaches a critical temperature, the film layer 24 will shrink lengthwise by a substantial amount, causing outer layers 20 and 22 to form raised pleats 200 transverse to the length direction of tongue 14, as shown in FIG. 8. Moreover, as a result of the formation of pleats 200, tongue 14 has a thickness after sterilization which is significantly greater than its thickness prior to sterilization. For example, depending on the materials used for layers 20, 22 and 24 and the adhesive layers therebetween, tongue 14 may have an initial thickness of about 0.015 inches, and a thickness after a sterilization process of about 2 times to more than about 10 times the initial thickness.

As a result of this shrinking and pleating action, tongue 14 has a length after sterilization which is significantly less than its length prior to sterilization. Preferably, the length of tongue 14 after sterilization is at least about 25% less than its original length; more preferably, at least about 40% less than its original length. The absolute amount of shrinkage of tongue 14 in the assembled position on latch mechanism 106 is not critical, however, as the presence of side 156 of operating handle 150 may interfere with and lessen somewhat the overall shrinkage of tongue 14. That is, under the same processing conditions, tongue 14 may exhibit a greater degree of shrinkage when it is standing alone and not assembled to the latch mechanism than when it is assembled to the latch mechanism. Despite these shrinkage forces, tongue 14 remains connected to body portion 12 both at end portion 26 and at end 40.

While not wishing to be held to any particular theory, it is believed that, at the critical shrinkage temperature, the adhesive layers 36 and 38 holding outer layers 20 and 22 to inner layer 24 soften. This softening permits alternating regions of outer layers 20 and 22 to pull away from inner layer 24 so as to form pleats 200 to accommodate the differential shrinkage between layer 24 on the one hand and layers 20 and 22 on the other hand.

Since the end 40 of tongue 14 remains adhered to body portion 12 throughout the sterilization procedure and after, the reduction in the length of tongue 14 may cause the tongue to have a tight fit around side 156 of operating handle 150. The shrinkage of tongue 14 during the sterilization process, however, is not so much as will cause tongue 14 to become severed from body portion 12 at gap 32. Subsequent to sterilization, seal 10 provides a visual indication of sterilization both in the appearance of pleats 200 on tongue 14 and in the color change of the sterilization indicating material in region 16.

As noted above, the amount by which tongue 14 desirably shrinks during the sterilization process depends upon the initial length of the tongue as well as the structure of the latch mechanism with which seal 10 is used. For latch mechanism 106 described above, tongue 14 should have an initial length which will allow it to easily reach from aperture 194 around side 156 of operating handle 150 for attachment to body portion 12 of the seal. After the sterilization procedure, however, tongue 14 desirably has a length which is too short to be assembled in this way. That is, tongue 14 should shrink by a sufficient amount that, if seal 10 is processed by itself through a sterilization cycle (i.e., not assembled to a sterilization container), tongue 14 should have a length which is too short to reach from aperture 194 around side 156 of operating handle 150 for attachment to body portion 12.

When used as described above, seal 10 serves as a reliable indicator as to whether container 100 has been tampered with subsequent to sterilization. Since the sterilization indicating material is provided on body portion 12 of seal 10, the entire seal must be processed through a sterilization treatment in order for the seal to indicate that sterilization has been completed. However, because of the shrinkage of tongue 14, seals 10 cannot be "precooked" through a sterilization cycle and later assembled to an unsterilized container or to a sterilized container which had been opened and which therefore had lost its sterile integrity. The use of seals 10 therefore eliminates subversive activities intended to create the impression that a container has been sterilized when it has not, or that a sterilized container has not been opened following sterilization.

As discussed previously, in order to open container 100 so as to gain access to its contents, operating handle 150 must be moved in an upward direction away from latch plate 166, causing the latch plate to move downwardly at least until hook members 182 and 184 thereof became disengaged from hook members 118 and 120 on receptacle 102. Since tongue 14 fits tightly around operating handle 150 subsequent to the sterilization process, any movement of operating handle 150 upwardly and away from latch plate 166 will separate tongue 14 from body portion 12 as the portion of layer 20 within gap 32 is pulled against and severed by the edge of aperture 194, all of which can be seen in FIG. 9. Thus, any attempt to open sterilization container 100 subsequent to a sterilization process will be revealed visually by the separation of one end of tongue 14 from the body portion of the seal.

In a variant of seal 10 described above, tongue 14 may consist solely of layer 24 of a high shrink film. In accordance with such embodiment, layer 24 would be adhered at one end directly to body portion 12, and would include a layer of adhesive 42, preferably a high temperature adhesive, at its free end. Such a seal would be used in the same manner as seal 10 described above. For some materials which shrink by a large amount, however, the rapid shrinkage during sterilization may cause the material to separate from body portion 12, resulting in failure of the seal. In those cases, outer layer 20 may overcome the problem by eliminating the direct connection of layer 24 to body portion 12. The same problem may arise at the free end 40 of tongue 14. That is, without the use of outer layer 22, the large amount of shrinkage of certain materials may cause the tip 40 of tongue 14 to separate from body portion 12 during sterilization. Layer 22 may prevent such separation by acting as a non-shrinking barrier layer which remains adhered to body portion 12 as the shrinkage layer shrinks.

Figure 10A:
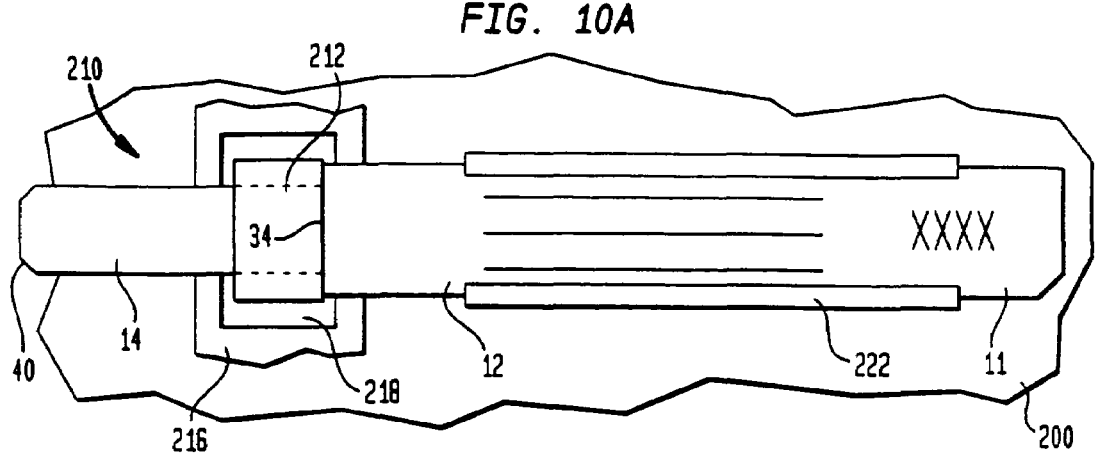
FIG. 10A is an enlarged elevational view showing an alternate use of the seal of FIG. 2 prior to a sterilization procedure.
Figure 10B:
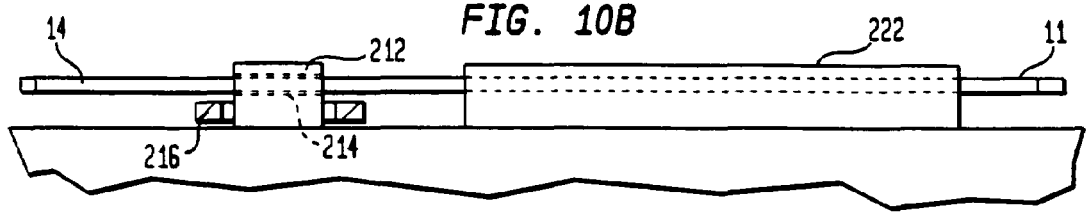
FIG. 10B is an enlarged top view showing the use of the seal depicted in FIG. 10A.

In another embodiment of the present invention, advantage is taken of the change in thickness of tongue 14 which takes place during the sterilization process. In accordance with this embodiment, the sterilization container may have a conventional hasp-type locking system which may form part of the latch mechanism for holding the lid of the container to the receptacle thereof, or which may be separate therefrom. Thus, referring to FIGS. 10A and 10B, the container 200 may have a latch mechanism 210 including a projecting member 212 with a generally rectangular aperture 214 therein. Aperture 214 has a length which is large enough to receive tongue 14 therethrough, but small enough to prevent the passage of body portion 12. The width of aperture 214 preferably is only slightly greater than the thickness of tongue 14 prior to sterilization. A hinged latch 216 is provided with an opening 218 therein for receiving projecting member 212 therethrough in a closed position of the latch mechanism. Projecting member 212 may be connected to one of the receptacle or lid of the container, while latch 216 may be connected to the other of the receptacle or lid, such that, in a latched position, the lid is locked in engagement with the receptacle. Alternatively, both projecting member 212 and latch 216 may be connected to the receptacle (or lid), with latch 216 having a structure (not shown) for engaging a corresponding structure on the lid (or receptacle) to prevent the removal of the lid from the receptacle in the latched position of the latch mechanism.

In either event, with latch mechanism 210 in the latched position, a tamper-proof seal 11 in accordance with the present invention may be inserted into the slot of a tag holder 222 alongside the latch mechanism so that tongue 14 thereof passes through the rectangular aperture 214 in projecting member 212. Seal 11 may be the same as seal 10 described above, except that the free end 40 of tongue 14 does not include an adhesive layer 42. Seal 11 may be advanced in tag holder 222 until end 34 of body portion 12 abuts projecting member 212.

Figure 11A:
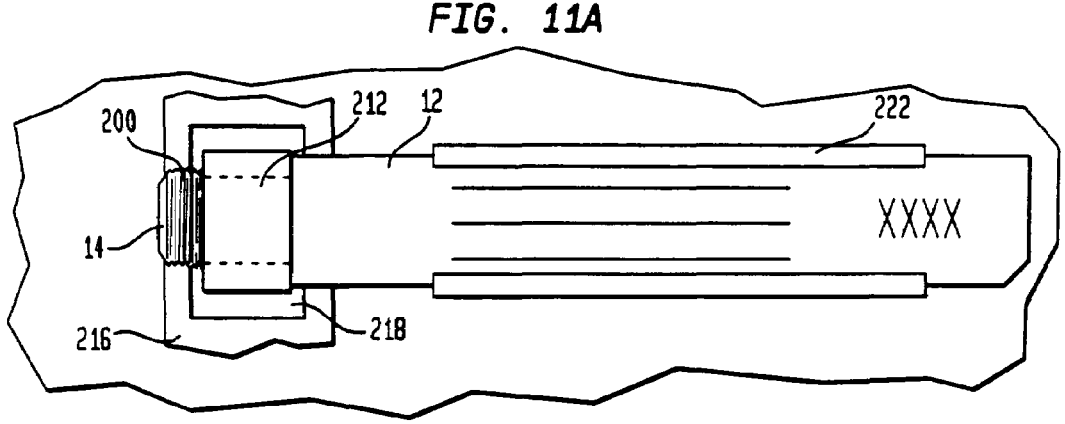
FIG. 11A is a view similar to FIG. 10A, showing the seal of FIG. 2 subsequent to a sterilization procedure.
Figure 11B:
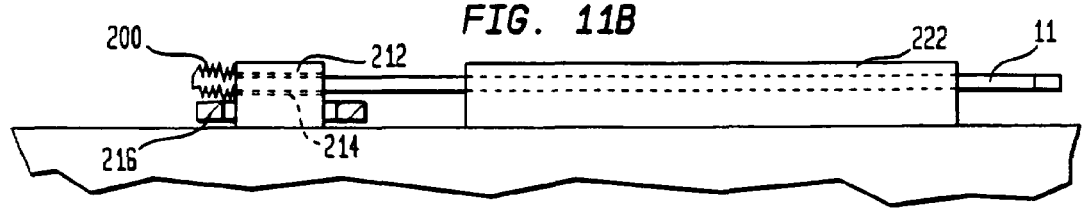
FIG. 11B is an enlarged top view showing the use of the seal depicted in FIG. 11A subsequent to a sterilization procedure.

With seal 11 assembled in latch mechanism 210 as described, container 200 is ready for a sterilization process. As with seal 10 described above, when the sterilization process reaches a critical temperature, the film layer 24 in seal 11 will shrink lengthwise causing outer layers 20 and 22 to form raised pleats 200 transverse to the length direction of tongue 14, as shown in FIGS. 11A and 11B. The formation of pleats 200 causes tongue 14 to have a post-sterilization thickness which is substantially greater than the thickness of tongue 14 prior to sterilization. Desirably, the increased thickness of tongue 14 is greater than the width of aperture 214, such that seal 11 cannot be removed from latch mechanism 210 without severing tongue 14 from body portion 12 at gap 32. Therefore, any attempt to open sterilization container 200 subsequent to a sterilization process would be revealed visually by the separation of tongue 14 from the body portion of the seal.

The use of seal 11 as described above provides a reliable mechanism for determining whether container 200 has been tampered with subsequent to sterilization. Since the sterilization indicating material is provided on body portion 12 of seal 11, the entire seal must be processed through a sterilization cycle in order for the seal to indicate that sterilization has occurred. However, any attempt to "precook" seals 11 for subsequent assembly to an unsterilized container or to a sterilized container previously opened will result in the shrinkage of tongue 14 with a concurrent increase in the tongue's thickness. As a result of this increased thickness, tongue 14 will no longer fit through aperture 214, and therefore cannot be applied to container 200 to create the impression either that the container has been sterilized when it has not, or that a sterilized container has not been opened subsequent to sterilization.

Figure 12:
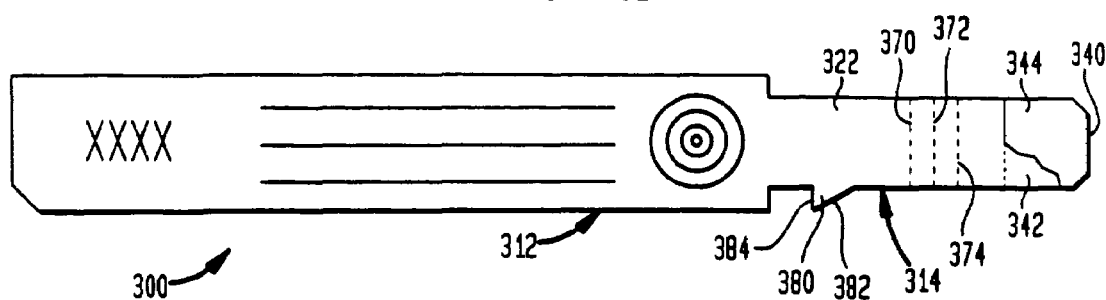
FIG. 12 is a front elevational view of a second embodiment of the seal of the present invention.
Figure 13:
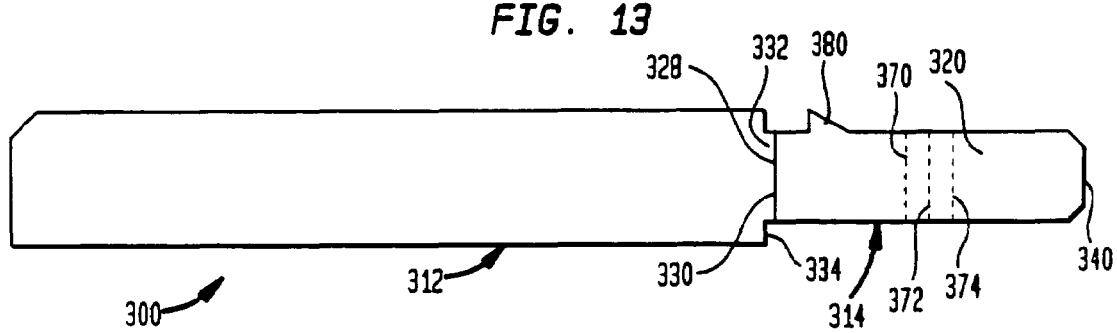
FIG. 13 is a rear elevational view of the seal of FIG. 12.
Figure 14:
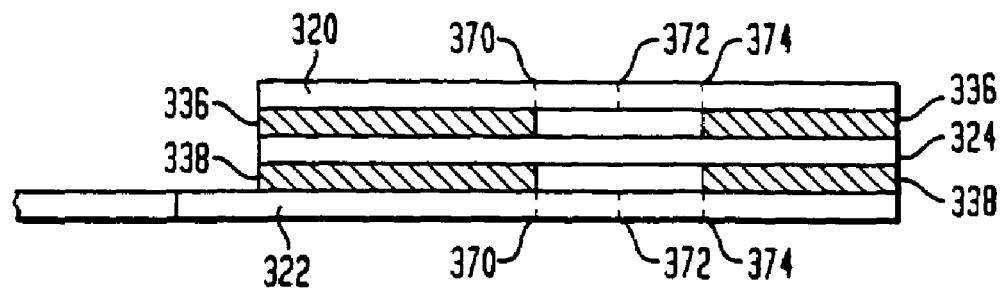
FIG. 14 is an enlarged partial side view of the seal of FIG. 12 showing the layers forming the tongue portion thereof.

A second preferred embodiment of a tamper-proof seal 300 in accordance with the present invention is illustrated in FIGS. 12-14. Seal 300 generally includes a body portion 312 and a severable tongue 314 projecting from one end thereof. Body portion 312 is substantially the same as body portion 12 of seal 10 discussed above. Tongue 314 is preferably a multiply laminate consisting of a pair of outer layers 320 and 322 sandwiching an inner layer 24 of a high shrinkage material. Preferably, layer 322 is simply a continuation of the material forming body portion 312.

Layer 324 is preferably formed from the same high shrinkage material as those described above for forming layer 24. Similarly, outer layer 320 may be formed from the same inert, flexible materials used to form outer layer 20 of seal 10. Preferably, layers 320, 322 and 324 each have one end which is coextensive with the free end 340 of tongue 314. The second end 328 of outer layer 320 and the second end 330 of inner layer 324 preferably terminate at a small spaced distance from the end 334 of body portion 312 so as to define a gap 332 therebetween. Gap 332 provides a weakened region enabling tongue 314 to be separated from body portion 312 following a sterilization procedure. Alternatively, the ends 328 and 330 of layers 320 and 324 may extend to or beyond the end 334 of body portion 312, and a series of perforations (not shown) may be formed in tongue 314 adjacent end 334 of body portion 312 to facilitate the separation of tongue 314 from the body portion of seal 300. Of course, gap 332 may also include perforations to make it easier to separate tongue 314 from body portion 312.

At about its midpoint, tongue 314 includes a series of perforations 370, 372 and 374 which extend across the width of the tongue. Perforations 370, 372 and 374 extend through outer layers 320 and 322, but preferably not through inner layer 324. Moreover, the perforations 370, 372 and 374 in outer layer 320 preferably are in registry with the perforations 370, 372 and 374 in outer layer 322. The purpose of perforations 370, 372 and 374 will be discussed below. It will be appreciated from that discussion that the perforations need not be formed at or near the midpoint of tongue 314, but may be formed at any point along the length of the tongue at some spaced distance from end 334 of body portion 312 and the free end 340 of the tongue.

Layers 320 and 322 may be laminated to layer 324 by adhesive layers 336 and 338, respectively. Layers 336 and 338 may be provided as integral adhesive coatings on the surface of layers 320, 322 and/or 324, or may be formed from a separate adhesive material capable of bonding layers 320 and 322 to layer 324. In either case, the adhesive should maintain its adhesive properties when exposed to the temperature and environmental conditions of the sterilization process, or at least prevent layers 320 and 322 from separating from layer 324. An example of an adhesive which may be useful for this purpose is a pressure sensitive acrylic adhesive.

Adhesive layer 336 is provided in all regions between outer layer 320 and inner layer 324, except for the region between perforations 370 and 374. Similarly, adhesive layer 338 is provided in all regions between outer layer 322 and inner layer 324, except for the region between perforations 370 and 374. The lack of adhesive between outer layers 320 and 322 and inner layer 324 in the region between perforations 370 and 374 allows the outer layers to move relative to the inner layer in this region and to separate therefrom as the inner layer shrinks during a sterilization procedure.

Near end 334 of body portion 312, one longitudinal edge of tongue 314 may be provided with a tapered projection 380. Projection 380 is defined by an inclined surface 382 and an abutment surface 384. As will be explained below, projection 380 helps to maintain seal 300 in assembled relationship to a sterilization container as the sterilization container is processed through a sterilization cycle.

Outer layer 322 adjacent the free end 340 of tongue 314 may include a layer of an adhesive 342 for adhering end 340 to body portion 312 in the use condition of seal 300. Adhesive 342 preferably is the same as or similar to adhesive 42 described above.

Seal 300 may be used in conjunction with sterilization container 100 in the same manner as seal 10 described above. Thus, once medical instruments or other articles to be sterilized have been placed in sterilization container 100 and latch mechanisms 106 have been moved to the locked position, seal 300 may be assembled to the latch mechanism on one or both sides of the container. Seal 300 is assembled to the latch mechanism in the same way as seal 10, i.e., by guiding tongue 314 through aperture 194 of the container as the body portion 312 of the seal is slid into slot 190. Body portion 312 is advanced until its end 334 abuts tab 192. In this position, projection 380 will have passed through aperture 194, whereupon the interference of abutment surface 384 with tab 192 will hold seal 300 in place during the sterilization process.

Once seal 300 is assembled to latch plate 166, the release layer 344 at the free end 340 of tongue 314 may be removed, exposing the adhesive 342 thereunder, and the tongue may be folded around and over side 156 of operating handle 150, whereupon the free end of seal 300 may be adhered to the body portion 312 thereof. In this assembled position, tongue 314 fits loosely around side 156 of operating handle 150 such that there is a substantial amount of free space therebetween.

Figure 15:
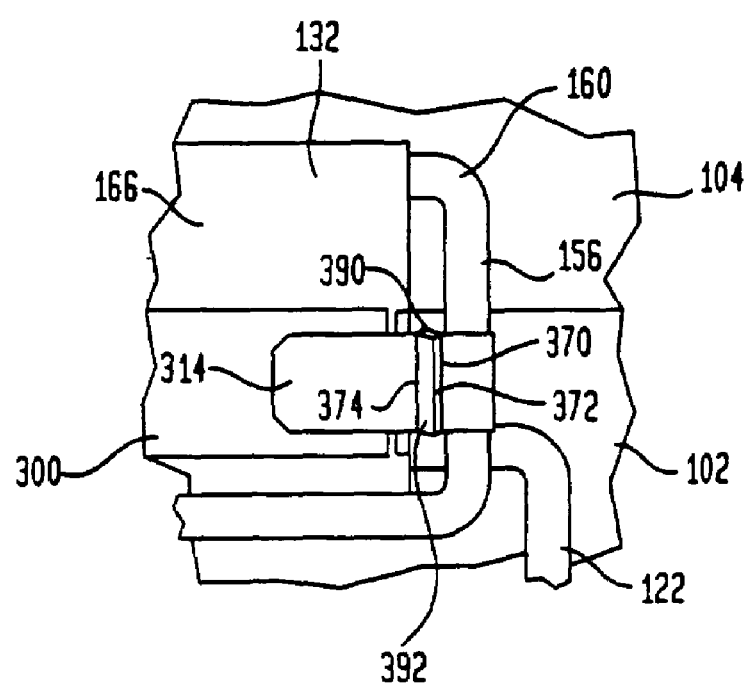
FIG. 15 is an enlarged view showing the seal of FIG. 12 on the sterilization container subsequent to a sterilization procedure.
Figure 16A:
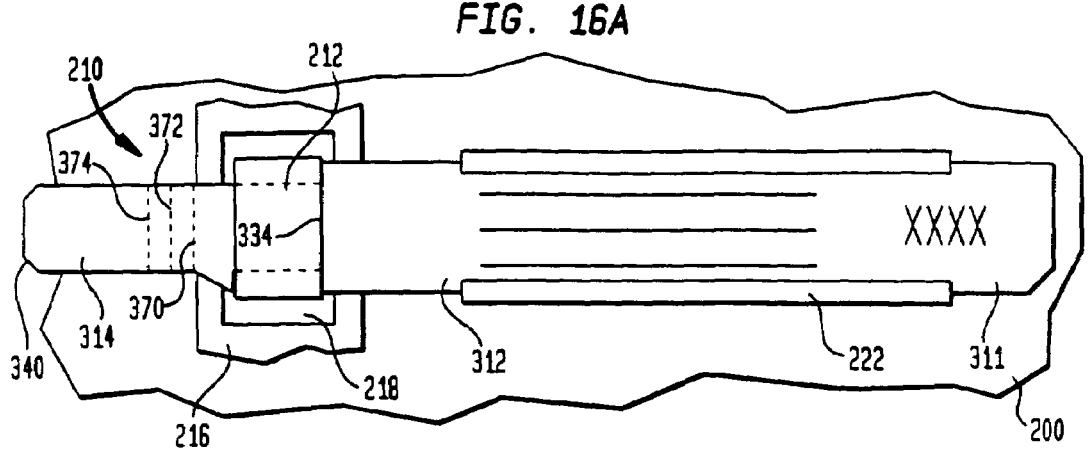
FIG. 16A is an enlarged elevational view showing an alternate use of the seal of FIG. 12 prior to a sterilization procedure.
Figure 16B:
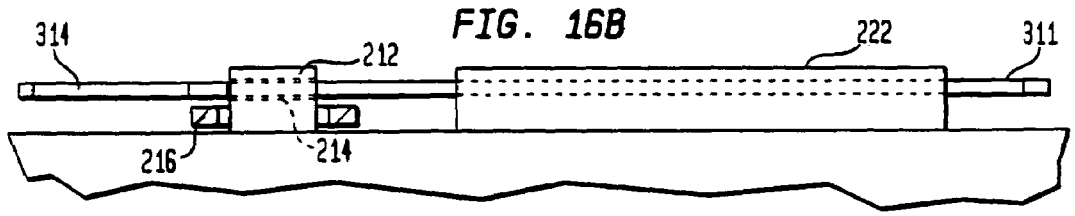
FIG. 16B is an enlarged top view showing the use of the seal depicted in FIG. 15A.

During a conventional sterilization process, film layer 324 will shrink lengthwise by a substantial amount. The force of this shrinkage causes outer layers 320 and 322 to deform outwardly along perforations 370, 372 and 374, as shown in FIG. 15, so as to form outwardly projecting pleats 390 and 392. As a result of this deformation, tongue 314 has a thickness in the region of pleats 390 and 392 which is significantly greater than the thickness of tongue 314 prior to sterilization. Additionally, as a result of this shrinkage process, tongue 314 has a length after sterilization which is significantly less than its length prior to sterilization. Since the end 340 of tongue 314 remains adhered to body portion 312 during and after the sterilization process, the reduction in the length of tongue 314 may cause the tongue to have a tight fit around side 156 of operating handle 150. The shrinkage of tongue 314 during the sterilization process, however, is not so much as will cause tongue 314 to become severed from body portion 312 at gap 332. Subsequent to sterilization, seal 300 provides a visual indication of sterilization both in the appearance of pleats 390 and 392 on tongue 314, and in the color change of any sterilization indicating material on body portion 312.

The amount by which tongue 314 shrinks during the sterilization process depends upon the initial length of the tongue as well as the structure of the latch mechanism with which seal 300 is used. For latch mechanism 106 described above, tongue 314 should have an initial length which will allow it to easily reach from aperture 194 around side 156 of operating handle 150 for attachment to body portion 312 of the seal. During sterilization, however, tongue 314 should shrink by a sufficient amount that, if seal 300 is processed by itself through a sterilization cycle, tongue 314 will be too short to reach from aperture 194 around side 156 of operating handle 150 for attachment to body portion 312. This is another feature which prevents seal 300 from being subjected to a sterilization process by itself and then assembled to a container that has not been sterilized or that has been contaminated.

When used as described above, seal 300 serves in the same manner as seal 10 to provide a reliable indication as to whether container 100 has been tampered with subsequent to sterilization. Furthermore, since tongue 314 following sterilization fits tightly around operating handle 150, any movement of operating handle 150 upwardly to open latch mechanism 106 will separate tongue 314 from body portion 312 as the portion of layer 322 within gap 332 is pulled against and severed by the edge of aperture 194. Thus, any attempt to open sterilization container 100 subsequent to a sterilization process will become visually apparent by the separation of one end of tongue 314 from the body portion 312 of the seal.

In another embodiment hereof, a tamper-proof seal 311 may be used in connection with sterilization containers having a conventional hasp-type locking mechanism such as the container 200 described above in connection with seal 10. Seal 311 may be the same as seal 300, except that the free end 340 of tongue 314 does not include an adhesive layer 342. With latch mechanism 210 of container 200 in the latched position, seal 311 may be inserted into the slot of tag holder 222 so that the tongue 314 thereof passes through the rectangular aperture 214 in projecting member 212. Seal 311 may be advanced in tag holder 222 until end 334 of body portion 312 abuts projecting member 212. The interference between projection 380 and projecting member 212 will hold seal 311 in this assembled position during the sterilization process.

Figure 17A:
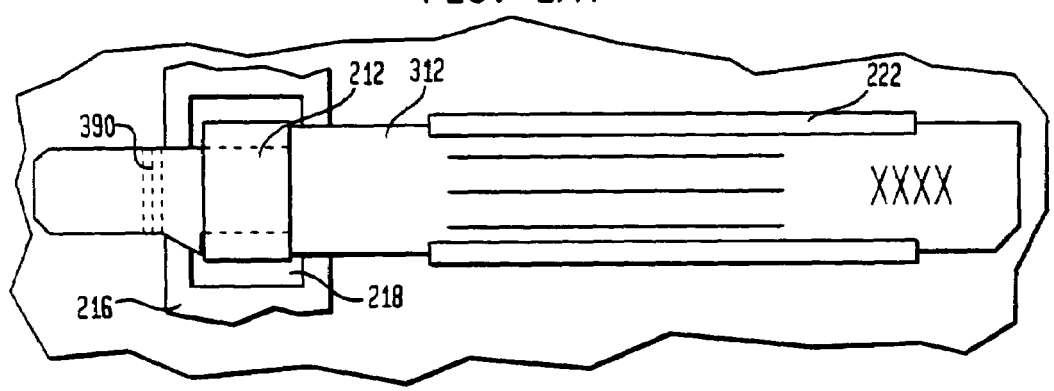
FIG. 17A is a view similar to FIG. 15A, showing the seal of FIG. 12 subsequent to a sterilization procedure.
Figure 17B:
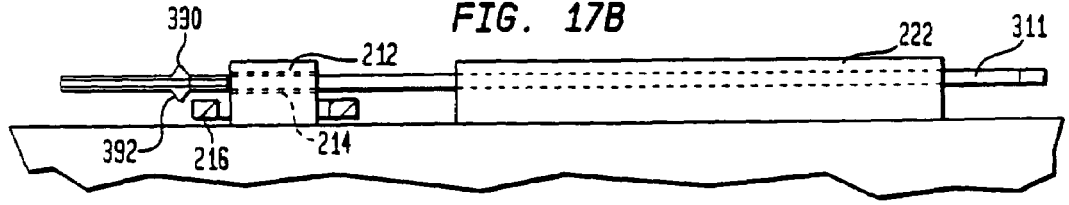
FIG. 17B is an enlarged top view showing the use of the seal depicted in FIG. 16A subsequent to a sterilization procedure.

After seal 311 has been assembled as described in latch mechanism 210, container 200 may be subjected to a sterilization process. When the sterilization process reaches a critical temperature, the film layer 324 in seal 311 will shrink lengthwise causing outer layers 320 and 322 to deform outwardly along perforations 370, 372 and 374 to form outwardly projecting pleats 390 and 392, as shown in FIGS. 17A and 17B. The formation of pleats 390 and 392 causes tongue 314 to have a post-sterilization thickness in the region of the pleats which is substantially greater than the thickness of tongue 314 prior to sterilization. The increased thickness of tongue 314 should be greater than the width of aperture 214, such that seal 311 cannot be removed from latch mechanism 210 without severing tongue 314 from body portion 312 at gap 332. Accordingly, any attempt to open sterilization container 200 subsequent to a sterilization process would be revealed visually by the separation of tongue 314 from the body portion of the seal.

The use of seal 311 as described in the foregoing provides a reliable mechanism for determining whether container 200 has been tampered with subsequent to a sterilization process. Since body portion 312 of seal 311 is provided with a sterilization indicating material, the entire seal must be processed through a sterilization cycle in order for the seal to indicate that sterilization has occurred. However, any attempt to "precook" seals 311 apart from a sterilization container will result in the shrinkage of tongue 314 with a concurrent increase in the tongue's thickness in the region of pleats 390 and 392. As a result of this increased thickness, tongue 314 will no longer fit through aperture 214, and therefore cannot be applied to an unsterilized container 200 to create the false impression that the container has been sterilized or that a sterilized container has not been opened subsequent to the sterilization process.

It will be appreciated that seal 300 need not include two outer layers 320 and 322 on opposite surfaces of inner layer 324, but rather could be formed with a single outer layer 322 arranged on one surface of layer 324. Such a seal would be used in the same manner as seal 300 described above. Similarly, seal 311 may be formed with only a single outer layer 322 on one surface thereof, provided that the pleat 390 formed during shrinkage of tongue 314 is sufficient in size to prevent the tongue from being removed from aperture 214 following a sterilization process.

Although the foregoing describes how seal 10 (and the other seals of the present invention) would be used in a conventional steam sterilization process, as noted at the outset hereof, the concept behind seal 10 may be used in connection with other known types of sterilization processes. It will be appreciated, of course, that modifications to the materials forming the seal may be needed in order to enable the seal to be used in these other processes. For example, where the seal is to be used in connection with an ultraviolet or gamma radiation sterilization process, layer 24 would be formed from a material known to exhibit a substantial amount of shrinkage upon exposure to such radiation. Also, a known sterilization indicating material appropriate for that sterilization process would be used. Similarly, for gas sterilization or gas plasma/hydrogen peroxide sterilization processes, layer 24 would be formed from a material known to exhibit a substantial amount of shrinkage during such processes, and a known sterilization indicating material appropriate to those processes would be used.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as set forth in the appended claims.

The invention claimed is:

1. A disposable seal for a container having a latch mechanism, comprising
   a body; and
   a tongue having one end connected to said body and a free end, said tongue including a layer of a material which shrinks under sterilization conditions, said shrinkable material having first and second surfaces;
   said tongue including at least one layer of a second material laminated to said first surface of said shrinkable material.

2. The disposable seal as claimed in claim 1, wherein said shrinkable material is a heat shrinkable material.

3. The disposable seal as claimed in claim 2, wherein said heat shrinkable material is a heat shrink vinyl.

4. The disposable seal as claimed in claim 1, further comprising a weakened region between said body and said tongue.

5. The disposable seal as claimed in claim 1, wherein said body includes a sterilization indicator material.

6. The disposable seal as claimed in claim 5, wherein said sterilization indicator material comprises a sterilization indicating ink.

7. The disposable seal as claimed in claim 1, wherein said tongue has an initial length and a post-sterilization length which is less than said initial length.

8. The disposable seal as claimed in claim 7, wherein said initial length of said tongue is sufficient to permit the tongue to be assembled to the latch mechanism in a use position, and said post-sterilization length of said tongue is insufficient to permit said tongue to be assembled to the latch mechanism in said use position.

9. The disposable seal as claimed in claim 1, further comprising an adhesive for adhering said free end of said tongue to said body.

10. The disposable seal as claimed in claim 1, wherein said second material includes a weakened region between said one end and said free end.

11. The disposable seal as claimed in claim 10, wherein said tongue has a longitudinal direction between said one end and said free end, and said weakened region includes a series of at least three perforations in said second material, said perforations extending in a direction transverse to said longitudinal direction.

12. The disposable seal as claimed in claim 11, further comprising an adhesive for adhering said second material to said shrinkable material, said adhesive being excluded from said weakened region.

13. The disposable seal as claimed in claim 1, wherein said tongue includes at least one layer of a third material laminated to said second surface of said shrinkable material.

14. The disposable seal as claimed in claim 13, wherein said second and third materials each include a weakened region between said one end and said free end.

15. The disposable seal as claimed in claim 14, wherein said tongue has a longitudinal direction between said one end and said free end, and said weakened regions include a series of at least three perforations in each of said second material and said third material, said perforations extending in a direction transverse to said longitudinal direction.

16. The disposable seal as claimed in claim 15, wherein said perforations in said second material are in registry with said perforations in said third material.

17. The disposable seal as claimed in claim 13, wherein said second and third materials are selected from the group consisting of polymers.

18. The disposable seal as claimed in claim 13, wherein said second material is the same as said third material.

19. The disposable seal as claimed in claim 18, wherein said second and third materials are selected from the group consisting of polyolefins.

20. The disposable seal as claimed in claim 1, wherein said tongue has an initial thickness and a post-sterilization thickness which is greater than said initial thickness.

21. The disposable seal as claimed in claim 1, wherein said second material is selected from the group consisting of polymers.

22. The disposable seal as claimed in claim 21, wherein said second material is selected from the group consisting of polyolefins.

23. The disposable seal as claimed in claim 1, wherein said tongue has a selected width, and said body has a width which is greater than said selected width.

24. A disposable seal for a container, comprising
   a body including a sterilization indicating ink; and
   a tongue having one end connected to said body and a free end, said tongue having an initial length and a post-sterilization length which is less than said initial length.

25. A disposable seal for a container, comprising
   a body including a sterilization indicator material; and
   a tongue having one end connected to said body and a free end, said tongue having an initial thickness and a post-sterilization thickness which is greater than said initial thickness.

* * * * *